United States Patent
Fitch et al.

(10) Patent No.: US 8,060,500 B1
(45) Date of Patent: Nov. 15, 2011

(54) METHOD AND SYSTEM FOR SELECTING A HEALTHCARE PROVIDER WITH MINIMAL OFFICE WAIT TIMES

(75) Inventors: Todd M. Fitch, Santa Clara, CA (US); Thomas Anthony Frasher, Sunnyvale, CA (US); Steven Sholtis, El Dorado Hills, CA (US); Sean P. Lewis, Dublin, CA (US)

(73) Assignee: Intuit Inc., Mountain View, CA (US)

( * ) Notice: Subject to any disclaimer, the term of this patent is extended or adjusted under 35 U.S.C. 154(b) by 968 days.

(21) Appl. No.: 12/018,076

(22) Filed: Jan. 22, 2008

(51) Int. Cl.
*G06F 7/00* (2006.01)
*G06F 17/00* (2006.01)

(52) U.S. Cl. .................. 707/724; 707/725; 707/732

(58) Field of Classification Search .............. 707/724, 707/725, 732, 999.003
See application file for complete search history.

(56) References Cited

U.S. PATENT DOCUMENTS

| | | | |
|---|---|---|---|
| 6,163,781 A * | 12/2000 | Wess, Jr. ............... | 707/999.103 |
| 6,389,454 B1 * | 5/2002 | Ralston et al. ........... | 709/204 |
| 6,647,328 B2 * | 11/2003 | Walker ................. | 701/2 |
| 2002/0128879 A1 * | 9/2002 | Spears ................ | 705/1 |
| 2005/0097188 A1 * | 5/2005 | Fish .................. | 709/217 |
| 2005/0159886 A1 * | 7/2005 | Kim ................... | 701/208 |
| 2006/0050849 A1 * | 3/2006 | Skaberna ............... | 378/118 |

* cited by examiner

*Primary Examiner* — Vincent Boccio
(74) *Attorney, Agent, or Firm* — Gunnison, McKay & Hodgson, L.L.P.; Philip McKay

(57) ABSTRACT

A method and system for selecting a healthcare provider includes a process for selecting a healthcare provider whereby healthcare provider list data is obtained, along with various data regarding the healthcare providers on the healthcare provider list, and the data is stored in a healthcare provider database. When a healthcare consumer initiates a healthcare provider search request, one or more healthcare consumer criteria for acceptable/desired healthcare providers and/or healthcare services needed is obtained and used to search the healthcare provider database to identify one or more healthcare providers most closely meeting the healthcare consumer's criteria. The availability of appointments and/or estimated wait times for the identified one or more healthcare providers are then obtained. The healthcare consumer is then provided information regarding the one or more identified healthcare providers along with the available appointments and/or estimated office wait times for the one or more identified healthcare providers.

25 Claims, 2 Drawing Sheets

METHOD AND SYSTEM FOR SELECTING A HEALTHCARE PROVIDER WITH MINIMAL OFFICE WAIT TIMES

BACKGROUND

Most healthcare consumers have local healthcare providers that they regularly use for obtaining healthcare services in and/or around their city of residence. Typically, healthcare consumers know where these local provider's offices/facilities are located along with various other information about a given local healthcare provider such as, but not limited to: whether the healthcare provider is in the healthcare consumer's healthcare insurance plan network and/or program, i.e., is a preferred provider for the healthcare consumer's healthcare insurance plan network and/or program; how much the healthcare provider charges; contact information for the healthcare provider such as phone number and address; the types of services provided by the healthcare provider; the fastest way to get to the healthcare provider's office/facilities; and, in many cases, how long the average wait time is for a given healthcare provider.

While the situation described above works quite well for healthcare consumers needing healthcare services in their local area from healthcare providers they regularly use, there are many instances where a healthcare consumer may need a healthcare provider other than their familiar local area healthcare providers. For instance, an injury or illness may occur while away from home. Likewise, prescriptions, medications and equipment may be needed while the healthcare consumer is away from home. In addition, a healthcare consumer may need to know the closest healthcare provider to the healthcare consumer's present location that can address the healthcare consumer's specific need, i.e., a specialist not normally or previously used by the healthcare consumer such as an allergist, surgeon, physical therapist, or other medical and/or therapy specialist. As another example, a healthcare provider may move, or retire, or a healthcare consumer may change healthcare insurance plans/networks. In any of these cases, the healthcare consumer may need to find new healthcare providers even in their area of residence.

In addition to wishing to obtain relatively immediate information about healthcare providers in, or around, a specific location, in many instances, healthcare consumers would like know the availability of appointments with a given healthcare provider and/or the wait time at a given healthcare provider's office between the scheduled appointment times and the times when patients are actually being seen.

In short, in many, if not most, instances, a healthcare consumer would like to know not only the closest healthcare provider in terms of time and/or distance, but also the healthcare provider that has the soonest available appointment and/or the shortest wait time in order to choose the healthcare provider offering the quickest opportunity for the healthcare consumer to actually receive healthcare services.

SUMMARY

In accordance with one embodiment, a method and system for selecting a healthcare provider includes a process for selecting a healthcare provider whereby, in one embodiment, a healthcare provider list is obtained and, in one embodiment, data representing the healthcare provider list, and/or various data regarding the healthcare providers on the healthcare provider list, is stored in a healthcare provider database that is local, remote, or a combination of local and remote. In one embodiment, a healthcare consumer initiates a healthcare provider search request. In one embodiment, the healthcare provider search request includes one or more healthcare consumer criteria for acceptable/desired healthcare providers and/or healthcare services needed. In one embodiment, the healthcare provider search request, and/or one or more healthcare consumer criteria for acceptable/desired healthcare providers and/or healthcare services needed, is then used to search the healthcare provider database to identify one or more healthcare providers most closely meeting the healthcare consumer's criteria at the time of the request. In one embodiment, the availability of appointments and/or estimated wait times for one or more of the one or more healthcare providers most closely meeting the healthcare consumer's criteria at approximately the time of the request is obtained. In one embodiment, the healthcare consumer is then provided information regarding one or more identified healthcare providers meeting, or coming closest to meeting, the healthcare consumer's healthcare provider criteria, along with the available appointment data and/or estimated office wait time data for the one or more identified healthcare providers.

In one embodiment, all, or part, of the data representing the healthcare provider list, and/or various data regarding the healthcare providers on the healthcare provider list, is obtained from, and/or is based on, information obtained by process for selecting a healthcare provider via healthcare consumer input into a computing system through a healthcare consumer interface device, such as a keyboard, mouse, touch pad, voice recognition software, or any other means and/or mechanism for converting healthcare consumer actions into computing system processes and/or otherwise entering data into a computing system implementing at least part of the process for selecting a healthcare provider.

In one embodiment, all, or part, of the data representing the healthcare provider list, and/or various data regarding the healthcare providers on the healthcare provider list, is obtained from, and/or is based on, information obtained by the process for selecting a healthcare provider from one or more healthcare insurance plan sources such as, but not limited to: web-sites; databases associated with and/or controlled by the healthcare insurance plan; computer program products available from the healthcare insurance plan; or various other healthcare insurance plan sources. In one embodiment, the information obtained from one or more healthcare insurance plan sources includes listings of "in-network" and/or preferred providers and/or ratings of healthcare providers supplied by other plan participants and/or the healthcare insurance plan provider.

In one embodiment, all, or part, of the data representing the healthcare provider list, and/or various data regarding the healthcare providers on the healthcare provider list, is obtained from, and/or is based on, information obtained by the process for selecting a healthcare provider from, or through, a computing system implemented data management system, program, package or application that is a parent system for, in communication with, or is associated with, the process for selecting a healthcare provider. In one embodiment, a computing system implemented data management system can be, but not limited to, a personal healthcare management, personal financial, business financial, accounting, or tax preparation data management system, program, package or application that implements, includes, is accessed by, and/or is otherwise associated with, the process for selecting a healthcare provider. In one embodiment, all, or part, of the data representing the healthcare provider list, and/or various data regarding the healthcare providers on the healthcare provider list, is then accessed by, and/or provided to, the process for selecting a healthcare provider by and/or though the computing system implemented data management system.

In one embodiment, all, or part, of the data representing the healthcare provider list, and/or various data regarding the healthcare providers on the healthcare provider list, is obtained from, and/or is based on, information obtained by the process for selecting a healthcare provider from web-sites and/or display screens using screen scraping technology, and/ or any similar data gathering technology whether known at the time of filing or as developed thereafter.

In one embodiment, all, or part, of the data representing the healthcare provider list, and/or various data regarding the healthcare providers on the healthcare provider list, is obtained from, and/or is based on, information obtained by process for selecting a healthcare provider from any combination of the above sources and/or from any other source of healthcare providers and/or data representing healthcare providers whether known at the time of filing or as developed thereafter.

In one embodiment, once the data representing the healthcare provider list, and/or various data regarding the healthcare providers on the healthcare provider list, is obtained by the process for selecting a healthcare provider, the data representing the healthcare provider list, and/or various data regarding the healthcare providers on the healthcare provider list is then stored in a healthcare provider database, portions of which can be a local, remote or combination local and remote database. In one embodiment, the healthcare provider database is a data storage device, a designated server system or computing system, or a designated portion of one or more server systems or computing systems, or a distributed database, or an external and/or portable hard drive, or any combination of the foregoing. In one embodiment, the healthcare provider database is a dedicated mass storage device implemented in software, hardware, or a combination of hardware and software. In one embodiment, the healthcare provider database includes a web-based function accessible through a private and/or public network and/or Internet connection. In one embodiment, the healthcare provider database is a computer program product.

In one embodiment, the healthcare consumer initiates a healthcare provider search request using a computing system. Herein a computing system can be a desktop computer, a portable computer, a workstation, a two-way pager, a cellular telephone, a smart phone, a digital wireless telephone, a PDA, a server computer, an Internet appliance, or any other device that includes components that can execute all, or part, of a process for selecting a healthcare provider, and/or a computing system implemented data management system, and/or a global positioning satellite capability, in accordance with at least one of the embodiments as described herein. Similarly, a computing system may include multiple different computers, wireless devices, cellular telephones, digital telephones, two-way pagers, personal digital assistants, server computers, or any desired combination of these devices, that are coupled to perform the processes and/or operations as described herein.

In one embodiment, the healthcare consumer initiates a healthcare provider search request via connection to a network. In one embodiment, the network can be any network or network system that is of interest to a healthcare consumer such as, a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

In one embodiment, the healthcare provider search request initiated by the consumer includes one or more healthcare consumer criteria for acceptable/desired healthcare providers and/or healthcare services needed. In one embodiment, the healthcare consumer's healthcare provider criteria includes, and/or is based on, any healthcare consumer provided parameters/desires including, but not limited to, one or more of the following: healthcare providers closest to the healthcare consumer in terms of distance; healthcare providers closest to the healthcare consumer in terms of time; in terms of availability; healthcare providers in specific neighborhoods and/or parts of a city, or not in specific neighborhoods and/or parts of a city; healthcare providers that subscribe or belong to the healthcare consumer's healthcare insurance plan network, i.e. healthcare insurance plan preferred providers; healthcare providers having strong ratings from other healthcare consumers; healthcare providers having specific capabilities and/ or offering specific services; and/or any other healthcare consumer criteria and/or combination of criteria.

In one embodiment, at least part of the healthcare consumer's healthcare provider search request and/or healthcare provider criteria are obtained by process for selecting a healthcare provider by healthcare consumer input into a computing system through a healthcare consumer interface and/or an interface device, such as a keyboard, mouse, touch pad, voice recognition software, or any other means and/or mechanism for converting healthcare consumer actions into computing system processes and/or otherwise entering data into a computing system implementing at least part of the process for selecting a healthcare provider.

In one embodiment, at least part of the healthcare consumer's healthcare provider criteria is obtained manually, semi-automatically, or automatically, by process for selecting a healthcare provider from one or more healthcare insurance plan sources such as, but not limited to: web-sites; databases associated with and/or controlled by the healthcare insurance plan; computer program products available from the healthcare insurance plan; or various other healthcare insurance plan sources. In one embodiment, the information obtained from one or more healthcare insurance plan sources includes listings of "in-network" and/or preferred providers and/or ratings of healthcare providers supplied by other plan participants, non-plan participants, and/or the healthcare insurance plan provider, and/or any combination thereof.

In one embodiment, at least part of the healthcare consumer's healthcare provider criteria is obtained manually, semi-automatically, or automatically, by process for selecting a healthcare provider from, or through, a computing system implemented data management system, program, package or application that is a parent system for, is in communication with, or is associated with, the process for selecting a healthcare provider.

In one embodiment, at least part of the healthcare consumer's healthcare provider criteria is obtained from web-sites and/or display screens using screen scraping technology.

In one embodiment, at least part of the healthcare consumer's healthcare provider criteria is obtained by the process for selecting a healthcare provider from the healthcare consumer's personal health record data and/or a previously filled in health profile.

In one embodiment, at least part of the healthcare consumer's healthcare provider criteria is obtained by the process for selecting a healthcare provider from any combination of the above sources and/or from any other source of healthcare consumer criteria data, whether known at the time of filing or as developed thereafter.

In one embodiment, the healthcare consumer's healthcare provider criteria includes healthcare provider criteria based on the position of the healthcare provider relative to a given location, such as the healthcare consumer's present location. In one embodiment, a healthcare consumer's present location is obtained by process for selecting a healthcare provider by healthcare consumer input into a computing system through a healthcare consumer interface device. In one embodiment, a healthcare consumer's present location is provided by a computing system having a global positioning satellite capability, or other positioning technology.

In one embodiment, once the healthcare consumer's healthcare provider search request and/or healthcare provider criteria is obtained, data representing the healthcare consumer's healthcare provider criteria is then used to search the healthcare provider database to identify healthcare providers most closely meeting the healthcare consumer's criteria, and/or that are on the healthcare consumer's preferred healthcare provider list, at the time of the search request/need.

In one embodiment, the healthcare consumer's healthcare provider criteria data is made available to search the healthcare provider database at the time of the search request/need via data transfer from a computing system capable of transmitting data. In one embodiment, the healthcare consumer's healthcare provider criteria data is made available to search the healthcare provider database at the time of the search request/need via a network or network system.

In one embodiment, the healthcare consumer's healthcare provider criteria data is made available to search the healthcare provider database at the time of the search request/need by storing the healthcare consumer's healthcare provider criteria data on a healthcare consumer's healthcare provider criteria database and then providing for communication and/or data transfer between the healthcare consumer's healthcare provider criteria database and the healthcare provider database at the time of the search request/need. In one embodiment, the healthcare consumer's healthcare provider criteria database is a data storage device, a designated server system or computing system, or a designated portion of one or more server systems or computing systems, or a distributed database, or an external and/or portable hard drive. In one embodiment, the healthcare consumer's healthcare provider criteria database is a dedicated mass storage device implemented in software, hardware, or a combination of hardware and software. In one embodiment, the healthcare consumer's healthcare provider criteria database is a web-based function.

In one embodiment, the healthcare consumer's healthcare provider criteria is made available to search the healthcare provider database at the time of the search request/need via a computer program product as defined herein, such as, but not limited to, a data storage disk or memory stick, and providing the healthcare provider database access to the computer program product.

In one embodiment, once the healthcare consumer's healthcare provider criteria is made available to search the healthcare provider database, and one or more healthcare providers are identified that most closely meet the healthcare consumer's criteria, the availability of appointments and/or estimated wait times for one or more of the one or more healthcare providers most closely meeting the healthcare consumer's criteria at the time of the request is obtained from the one or more healthcare providers meeting, or most closely meeting, the healthcare consumer's criteria.

In one embodiment, the availability of appointments and/or estimated wait times for one or more of the one or more healthcare providers meeting, or most closely meeting, the healthcare consumer's criteria is obtained by a process for selecting a healthcare provider from a computing system implemented data management system that provides the healthcare provider's offices/employees with a capability to provide the process for selecting a healthcare provider data indicating next available appointments and/or estimated wait times.

In one embodiment, the next available appointment and/or estimated wait time data for a given healthcare provider is entered manually by one or more healthcare provider personal through an interface display using an interface device. In one embodiment, the next available appointment and/or estimated wait time data for a given healthcare provider is manually, semi-automatically, or automatically entered/determined based on one or more defined actions taken by one or more healthcare provider personal. In one embodiment, the next available appointment and/or estimated wait time data for a given healthcare provider is semi-automatically, or automatically, entered/determined based on one or more actions taken by one or more healthcare provider computing systems and/or computing system implemented applications, such as starting a timer or opening a designated file.

In one embodiment, the next available appointment and/or estimated wait time data for a given healthcare provider is entered/determined by allowing process for selecting a healthcare provider access to one or more of the healthcare provider's computing systems and/or computing system implemented applications, such as a calendar/appointment application. In one embodiment, the next available appointment and/or estimated wait time data for a given healthcare provider is either transferred to the process for selecting a healthcare provider or to a data source accessible by the process for selecting a healthcare provider. In one embodiment, the next available appointment and/or estimated wait time data for a given healthcare provider is accessed by the process for selecting a healthcare provider on a computing system and/or database under the control of the healthcare provider.

In one embodiment, a given healthcare provider indicates that certain conditions are given priority in their office. For instance, a given healthcare provider may indicate that patients having AIDS related conditions will be given first priority.

In one embodiment, the healthcare consumer is then provided information regarding one or more identified healthcare providers meeting, or coming closest to meeting, the healthcare consumer's healthcare provider criteria, along with the available appointment data and/or estimated office wait time data for the one or more identified healthcare providers through a computing system and/or a network.

In one embodiment, the healthcare consumer is then provided the opportunity to select one of the healthcare providers meeting, or coming closest to meeting, the healthcare consumer's healthcare provider criteria. In one embodiment, the healthcare consumer is then also provided the opportunity to select and schedule a specific appointment with one of the healthcare providers. In one embodiment, the healthcare consumer is provided the opportunity to select a healthcare provider and the next specific appointment with that healthcare provider is automatically scheduled with the selected healthcare provider. In one embodiment, the healthcare provider is automatically selected based on, the healthcare provider meeting, or coming closest to meeting, the healthcare consumer's healthcare provider criteria, and/or having the soonest available appointment, and/or the shortest wait time and the next specific appointment with that healthcare provider is automatically scheduled.

Using the method and system for selecting a healthcare provider disclosed herein, a list of healthcare providers and related healthcare provider information is created and stored in a healthcare provider database. Then when a healthcare service need arises, a healthcare consumer can use pre-defined or currently defined healthcare provider criteria data, and/or preferred healthcare provider list data, to search the healthcare provider database, at the time of need, to identify one or more healthcare providers meeting, or coming closest to meeting, the healthcare consumer's healthcare provider criteria in "real-time". In one embodiment, the healthcare consumer is then provided with next available appointment times and/or estimated wait times for one or more of the one or more healthcare providers meeting, or coming closest to meeting, the healthcare consumer's healthcare provider criteria. Consequently, using the method and system for selecting a healthcare provider disclosed herein, a healthcare consumer can determine not only the closest healthcare provider in terms of time and/or distance, but also the healthcare provider that has the soonest available appointment and the shortest wait time in order to choose the healthcare provider offering the quickest opportunity for the healthcare consumer to actually receive healthcare services.

As discussed in more detail below, using the below embodiments, with little or no modification and/or healthcare consumer input, there is considerable flexibility, adaptability, and opportunity for customization to meet the specific needs of various healthcare consumers under numerous circumstances.

Figure 1:
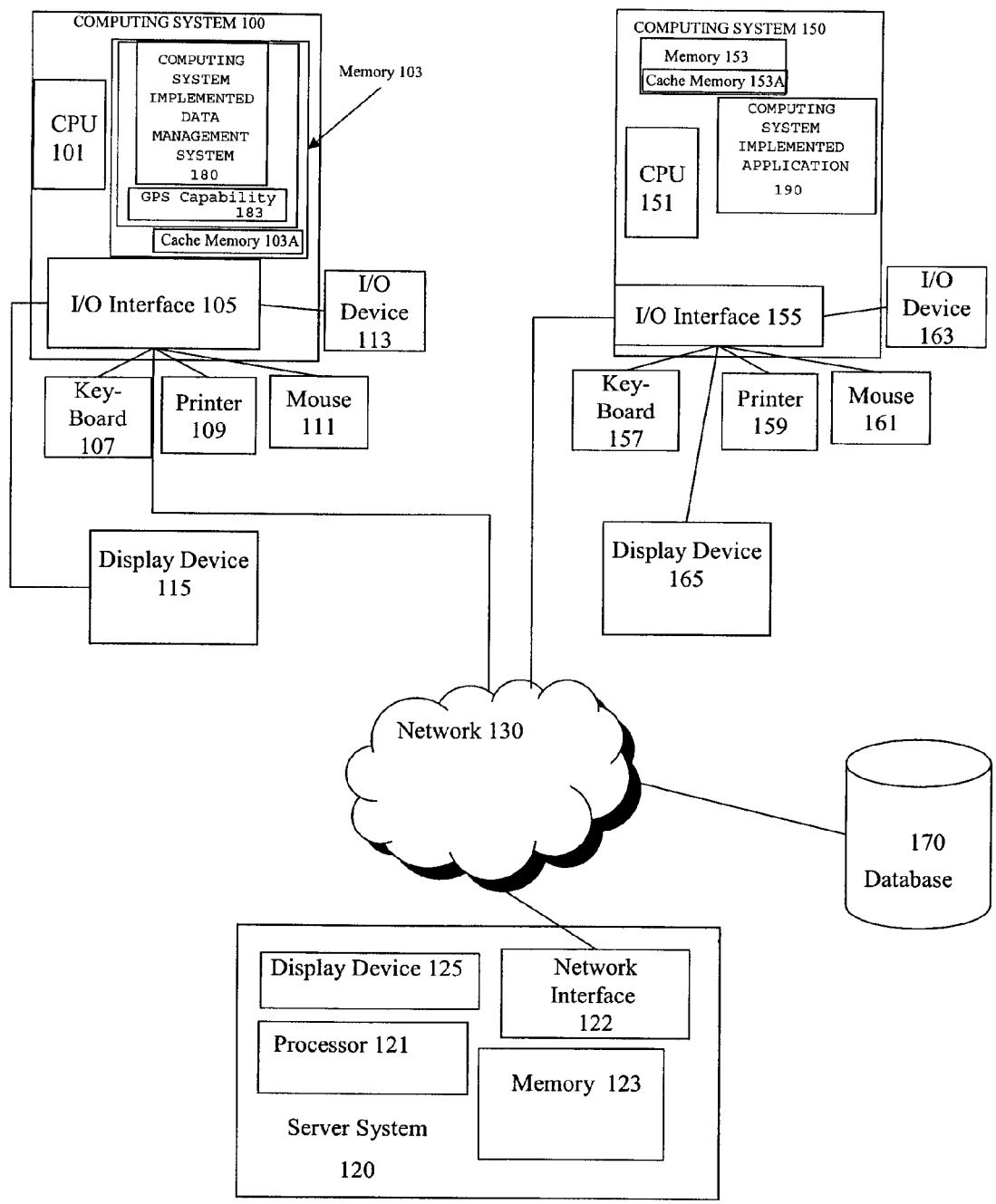
FIG. 1 is a block diagram of an exemplary hardware architecture for implementing one embodiment.

Common reference numerals are used throughout the FIG.s and the detailed description to indicate like elements. One skilled in the art will readily recognize that the above FIG.s are examples and that other architectures, modes of operation, orders of operation and elements/functions can be provided and implemented without departing from the characteristics and features of the invention, as set forth in the claims below.

DETAILED DESCRIPTION

Embodiments will now be discussed with reference to the accompanying FIG.s, which depict one or more exemplary embodiments. Embodiments may be embodied in many different forms and should not be construed as limited to the embodiments set forth herein, shown in the FIG.s, and/or described below. Rather, these exemplary embodiments are provided to allow a complete disclosure that conveys the principles of the invention, as set forth in the claims, to those of skill in the art.

Hardware System Architecture

FIG. 1 is a block diagram of an exemplary hardware architecture for implementing one embodiment of a system and method for selecting a healthcare provider, such as exemplary process 200 (FIG. 2) discussed herein, that, returning to FIG. 1, includes: a computing system 100, e.g., a first computing system; a computing system 150, e.g., a second computing system; a server system 120; and a database 170, all operatively coupled by a network 130.

As seen in FIG. 1, computing system 100 typically includes a central processing unit (CPU) 101, an input/output (I/O) interface 105, and a memory system 103, including cache memory 103A. In one embodiment, memory system 103 includes all, or part of, a computing system implemented data management system 180 such as, but not limited to: a computing system implemented healthcare management system; a computing system implemented personal financial management system; a computing system implemented business financial management system; a computing system implemented personal accounting system; a computing system implemented business accounting system; a computing system implemented tax preparation system; or any other computing system implemented personal and/or business data management system. In one embodiment, computing system implemented data management system 180 is stored, in whole, or in part, in memory system 103, and is used by, or includes, as discussed below, a process for selecting a healthcare provider, such as exemplary process 200 (FIG. 2) discussed below.

In one embodiment, computing system 100 is a portable, and/or handheld, and/or vehicle mounted, system including global positioning satellite (GPS) capability 183. In one embodiment, computing system 100 is a workstation, a two-way pager, a cellular telephone, a smart phone, a digital wireless telephone, a Personal Digital Assistant (PDA), a server computer, an Internet appliance, or any other device, or any desired combination of devices/systems, that includes a global positioning satellite capability 183. Herein a global positioning satellite capability, such as global positioning satellite capability 183 refers to the ability to receive signals from and/or communicate with global positioning satellites to determine a healthcare consumer's location. In addition, in many cases, a global positioning satellite capability, such as global positioning satellite capability 183, includes the ability to show a healthcare consumer's position relative to other locations, addresses and positions and to provide detailed directions to those other locations, addresses and positions either visually or in text form. In addition, a global positioning satellite capability, such as global positioning satellite capability 183, often includes the ability to provide detailed information about those other locations, addresses and positions such as addresses, phone numbers, e-mail addresses, web-sites, and other data associated with the other locations, addresses and positions. As discussed below, some, or all, or more, of these features are provided to, accessed by, relied upon by, and/or associated with, a system and method for selecting a healthcare provider, such as exemplary process 200 (FIG. 2) discussed herein, through a global positioning satellite capability of computing system 100 (FIG. 1), such as global positioning satellite capability 183.

As discussed in more detail below, in one embodiment, all, or part of, a process for selecting a healthcare provider, and/or a computing system implemented data management system, and/or a global positioning satellite capability, can be loaded, in whole, or in part, into computing system 100 for storage in memory system 103 and/or cache memory 103A.

Computing system 100 (FIG. 1) may further include standard user interface devices such as a keyboard 107, a mouse 111, a printer 109, and a display device 115, as well as, one or more standard input/output (I/O) devices 113, such as a compact disk (CD) or Digital Video Disc (DVD) drive, floppy disk drive, or other digital or waveform port, or other device capable of inputting data to, and outputting data from, computing system 100, whether available or known at the time of filing or as later developed. As discussed in more detail below, in one embodiment, a process for selecting a healthcare provider and/or a computing system implemented data management system are entered, in whole, or in part, into computing system 100 via I/O device 113, such as from a CD, DVD, floppy disk, portable hard drive, memory stick, download site, or other medium and/or computer program product as defined herein.

In one embodiment, computing system 100 is a computing system used and/or accessible by another computing system, such as computing system 150. In one embodiment, healthcare provider list data, healthcare consumer healthcare provider criteria data, healthcare provider appointment time and/or wait time data, results data, and/or any other process related data, are stored in and/or by computing system 100.

In one embodiment, computing system 150, is a computing system such as, but not limited to, a workstation, a two-way pager, a cellular telephone, a smart phone, a digital wireless telephone, a Personal Digital Assistant (PDA), a server computer, an Internet appliance, or any other device, or any desired combination of these devices, that includes components that can execute all, or part, of a process for selecting a healthcare provider, and/or a computing system implemented data management system, and/or a computing system implemented application in accordance with at least one of the embodiments as described herein.

Similar to computing system 100, computing system 150 typically includes a CPU 151, an input/output (I/O) interface 155, and a memory system 153, including cache memory 153A. Similar to computing system 100, computing system 150 may further include standard user interface devices such as a keyboard 157, a mouse 161, a printer 159, and a display device 165, as well as, one or more standard input/output (I/O) devices 163, such as a compact disk (CD) or DVD drive, floppy disk drive, or other digital or waveform port, or other device capable of inputting data to, and outputting data from, computing system 150, whether available or known at the time of filing or as later developed.

As noted above, in one embodiment, computing system 150 includes a computing system implemented application 190. In one embodiment computing system implemented application 190 can be, but is not limited to: a computing system implemented calendar application used by a healthcare provider; a computing system implemented patient appointment scheduling application used by a healthcare provider; a computing system implemented timer application used by a healthcare provider; a computing system implemented data processing application used by a healthcare provider; a computing system implemented healthcare record data processing application used by a healthcare provider; and/or any other a computing system implemented application used by any user. In one embodiment computing system implemented application 190 is capable of interfacing and/or exchanging data with one or more other computing systems, such as computing system 100 and/or server system 120, and/or one or more databases, such as database 170, and/or one or more computing system implemented data management systems, such as computing system implemented data management system 180, and/or a computing system implemented application 190 via a network, such as network 130.

In one embodiment, computing system 150 is a computing system used and/or accessible by another computing system, such as computing system 100. In one embodiment, healthcare provider list data, healthcare consumer healthcare provider criteria data, healthcare provider appointment time and/or wait time data, results data, and/or any other process related data, are stored in and/or by computing system 150.

Also shown in FIG. 1 is exemplary database 170. In one embodiment, database 170 is a data storage device, a designated server system or computing system, or a designated portion of one or more server systems or computing systems, such as computing systems 100, 150 and server system 120, or a distributed database, or an external and/or portable hard drive. In one embodiment, database 170 is a dedicated mass storage device implemented in software, hardware, or a combination of hardware and software. In one embodiment, database 170 includes a web-based function. As discussed in more detail below, in one embodiment, database 170 is under the control of the healthcare consumer, and/or the healthcare consumer's agents, and/or a process for selecting a healthcare provider, such as exemplary process 200 (FIG. 2), and/or a computing system implemented data management system, such as a computing system implemented data management system 180 (FIG. 1), and/or a computing system implemented application, such as computing system implemented application 190, and/or global positioning satellite capability, such as global positioning satellite capability 183.

In one embodiment, database 170 is used, controlled, and/or accessible by, a provider of and/or a system and processes for selecting a healthcare provider, such as process for selecting a healthcare provider 200 (FIG. 2), and healthcare provider list data, healthcare consumer healthcare provider criteria data, healthcare provider appointment time and/or wait time data, results data, and/or any other process related data, are stored in database 170. In one embodiment, database 170 is used, controlled, and/or accessible by a provider of and/or a computing system implemented data management system, such as computing system implemented data management system 180, and healthcare provider list data, healthcare consumer healthcare provider criteria data, healthcare provider appointment time and/or wait time data, results data, and/or any other process related data, are stored in database 170. In one embodiment, database 170 is used, controlled, and/or accessible by a healthcare provider, and/or a provider of, and/or a computing system implemented application, such as computing system implemented application 190. In one embodiment, database 170 is used, controlled, and/or accessible by a provider of and/or a global positioning satellite capability, such as global positioning satellite capability 193 and global positioning satellite data, and/or mapping data, and/or healthcare service provider data is stored on database 170. In one embodiment, computing systems 100 and 150, and database 170, are coupled to a server system 120, and/or each other, through network 130. In one embodiment, server system 120 typically includes a server system display device 125, a server system processor 121, a server system memory 123, and a server system network interface 122.

Network 130 can be any network or network system that is of interest to a healthcare consumer such as, a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

Those of skill in the art will readily recognize that the components shown in FIG. 1, such as computing systems 100 and 150, database 170, server system 120, and their respective components, are shown for illustrative purposes only and that architectures with more or fewer components can implement, and benefit from, the invention. Moreover, one or more components of computing system 100, computing system 150, database 170, and server system 120 may be located remotely from their respective system and accessed via network, as discussed herein. In addition, the particular type of, and configuration of, computing systems 100 and 150, database 170, and server system 120 are not relevant.

As discussed in more detail below, in one embodiment, a process for selecting a healthcare provider, such as process for selecting a healthcare provider 200 (FIG. 2), and/or a computing system implemented data management system, such as a computing system implemented data management system 180 (FIG. 1), and/or a computing system implemented application, such as computing system implemented application 190, and/or global positioning satellite capability, such as global positioning satellite capability 193, are stored, in whole, or in part, in memory system 103 and/or cache memory 103A, of computing system 100, and/or memory system 153 and/or cache memory 153A of computing system 150, and/or in server memory system 123 of server system 120 and/or in database 170, and executed on computing system 100 and/or computing system 150. As used herein, a memory refers to a volatile memory, a non-volatile memory, or any combination of the two.

Although a process for selecting a healthcare provider, such as process for selecting a healthcare provider 200 (FIG. 2), and/or a computing system implemented data management system, such as a computing system implemented data management system 180 (FIG. 1), and/or a computing system implemented application, such as computing system implemented application 190, and/or global positioning satellite capability, such as global positioning satellite capability 193, are sometimes referred to herein, alternatively, as a system, process, an application, a module, a program, a component of a software system, a component of a software package, a component of a parent system, a plug-in, or a feature of a parent system, this terminology is illustrative only. In some embodiments, a process for selecting a healthcare provider, such as process for selecting a healthcare provider 200 (FIG. 2), and/or a computing system implemented data management system, such as a computing system implemented data management system 180 (FIG. 1), and/or a computing system implemented application, such as computing system implemented application 190, and/or global positioning satellite capability, such as global positioning satellite capability 193, are capable of being called from an application or the operating system. In one embodiment, an application, process, or program is generally defined to be any executable code. Moreover, those of skill in the art will understand that when it is said that an application, process, or an operation takes some action, the action is the result of executing one or more instructions by a processor, such as CPUs 101 and 151, or server system processor 121. In one embodiment, execution of a process by CPU 101, CPU 151, or server system processor 121, results in the operations of an agent computer process (not shown) and/or a rule computer process (not shown).

In one embodiment, a process for selecting a healthcare provider, such as process for selecting a healthcare provider 200 (FIG. 2), and/or a computing system implemented data management system, such as a computing system implemented data management system 180 (FIG. 1), and/or a computing system implemented application, such as computing system implemented application 190, and/or global positioning satellite capability, such as global positioning satellite capability 193, are computer applications or processes and/or data implemented and/or run and/or stored, in full, or in part, in, or on, a computer program product. Herein, a computer program product comprises a medium and/or I/O device configured to store or transport computer readable code, whether available or known at the time of filing or as later developed. Some examples of computer program products are CDs, DVDs, ROM cards, floppy discs, magnetic tapes, computer hard drives, portable hard drives, flash memory, volatile and non-volatile memory sticks, servers on a network, such as server system 120 of FIG. 1, and signals transmitted over a network, such as network 130 of FIG. 1, or other media or process capable of delivering computer readable data representing computer readable code, whether available or known at the time of filing or as later developed. This medium may belong to a computing system, such as computing systems 100 and 150 of FIG. 1, described above. However, in some embodiments, the medium also may be removable and/or remote from the computing system.

For example, all, or part, of a process for selecting a healthcare provider, such as process for selecting a healthcare provider 200 (FIG. 2), and/or a computing system implemented data management system, such as a computing system implemented data management system 180 (FIG. 1), and/or a computing system implemented application, such as computing system implemented application 190, and/or global positioning satellite capability, such as global positioning satellite capability 193, may be stored in a memory that is physically located in a location, such as server system memory 123, or database 170, of FIG. 1, different from a computing system, such as computing systems 100 and/or 150 of FIG. 1, utilizing a process for selecting a healthcare provider, and/or a computing system implemented data management system, and/or a computing system implemented application. In one embodiment, all, or part, of a process for selecting a healthcare provider, and/or a computing system implemented data management system, and/or a computing system implemented application, and/or global positioning satellite capability, may be stored in a memory that is physically located, separate from the computing system's processor(s), such as CPUs 101 and 151 of FIG. 1, and the computing system CPUs can be coupled to the memory in a client-server system, such as server system 120 of FIG. 1, or, alternatively, via connection to another computer, such as computing systems 100, 150 of FIG. 1, via modems and analog lines, digital interfaces and a digital carrier line, or wireless or cellular connections.

In one embodiment, the computing systems and/or server systems, such as computing systems 100 and/or 150 and/or server system 120 of FIG. 1, running and/or utilizing and/or storing all, or part, of a process for selecting a healthcare provider, such as process for selecting a healthcare provider 200 (FIG. 2), and/or a computing system implemented data management system, such as a computing system implemented data management system 180 (FIG. 1), and/or a computing system implemented application, such as computing system implemented application 190, and/or global positioning satellite capability, such as global positioning satellite capability 193, is a portable computer, a workstation, a two-way pager, a cellular telephone, a smart phone, a digital wireless telephone, a PDA, a server computer, an Internet appliance, or any other device that includes components that can execute all, or part, of a process for selecting a healthcare provider, and/or a computing system implemented data management system, and/or a computing system implemented application, and/or a global positioning satellite capability, in accordance with at least one of the embodiments as described herein. Similarly, in another embodiment, a process for selecting a healthcare provider, and/or a computing system implemented data management system, and/or a computing system implemented application, and/or global positioning satellite capability, may be implemented on and/or run and/or stored on a computing system and/or server system that is comprised of multiple different computers, wireless devices, cellular telephones, digital telephones, two-way pagers, personal digital assistants, server computers, or any desired combination of these devices, that are coupled to perform the processes and/or operations as described herein.

Process

Herein, the terms "healthcare consumer", "consumer", and/or "user" are used interchangeably to denote any person, party, or parties, who interact with, use, or receive information from a process for selecting a healthcare provider, or for whom interaction with a process for selecting a healthcare provider is performed, and/or an authorized agent of any person, party, or parties, who interact with, use, or receive information from a process for selecting a healthcare provider, or for whom interaction with a process for selecting a healthcare provider is performed.

Herein, the term "healthcare provider" and/or "healthcare service provider" denotes any individual person, persons, agencies, institutions, organizations, businesses, and/or other entities that provide medical treatment, medications, therapy, advice, and/or equipment. For example, herein, the term "healthcare provider" includes, but is not limited to: doctors; nurses; technicians; therapists; pharmacists; counselors; alternative medicine practitioners; medical facilities; doctor's offices; hospitals; emergency rooms; clinics; urgent care centers; alternative medicine clinics/facilities; physical therapy clinics/facilities; and any other entity providing general and/or specialized treatment, assessment, maintenance, therapy, medication, and/or advice relating to all, or any portion of, a healthcare consumer's state of health, including but not limited to: general medical, specialized medical, surgical, dental, vision, psychological, and/or any other type of treatment, assessment, maintenance, therapy, medication, and/or advice.

Herein, the term "healthcare" includes any general and/or specialized treatment, assessment, maintenance, therapy, medication, and/or advice relating to all, or any portion of, a healthcare consumer's state of health, including but not limited to: general medical, specialized medical, surgical, dental, vision, psychological, and/or any other type of treatment, assessment, maintenance, therapy, medication, and/or advice.

Herein, the term "medical treatment" includes, but is not limited to: one or more medications and/or medication regimes; physical therapy; recommended dietary changes; recommended activity level changes; other lifestyle changes; and/or surgical procedures; and/or any prescribed and/or suggested regime, medication, treatment, activity, avoided activity, and/or program designed to improve, maintain, and/or slow the degradation of, a healthcare consumer's health.

Herein, the terms "healthcare insurance plan", "healthcare benefit plan" and "health insurance program" are used interchangeably to denote any policy, program, means and/or mechanism whereby a healthcare consumer is provided healthcare benefits and/or healthcare services and/or entitlements to any from of healthcare.

Herein, the terms "global positioning satellite" and "GPS" are used interchangeably.

Herein, the term database, such as used in the term "healthcare provider database", can include any data storage device, such as a memory, file, a designated server system or computing system, or a designated portion of one or more server systems or computing systems or a distributed database, or an external and/or portable hard drive that is local, remote, or a combination of local and remote, to a computing system and/or computing system implemented application and/or management system using and/or processing the data in the database.

In accordance with one embodiment, a method and system for selecting a healthcare provider includes a process for selecting a healthcare provider whereby, in one embodiment, a healthcare provider list is obtained and, in one embodiment, data representing the healthcare provider list, and/or various data regarding the healthcare providers on the healthcare provider list, is stored in a healthcare provider database. In one embodiment, a healthcare consumer initiates a healthcare provider search request. In one embodiment, the healthcare provider search request includes one or more healthcare consumer criteria for acceptable/desired healthcare providers and/or healthcare services needed. In one embodiment, the healthcare provider search request, and/or one or more healthcare consumer criteria for acceptable/desired healthcare providers and/or healthcare services needed, is then used to search the healthcare provider database to identify one or more healthcare providers most closely meeting the healthcare consumer's criteria at the time of the request. In one embodiment, the availability of appointments and/or estimated wait times for one or more of the one or more healthcare providers most closely meeting the healthcare consumer's criteria at the time of the request is obtained. In one embodiment, the healthcare consumer is then provided information regarding one or more identified healthcare providers meeting, or coming closest to meeting, the healthcare consumer's healthcare provider criteria, along with the available appointment data and/or estimated office wait time data for the one or more identified healthcare providers.

Figure 2:
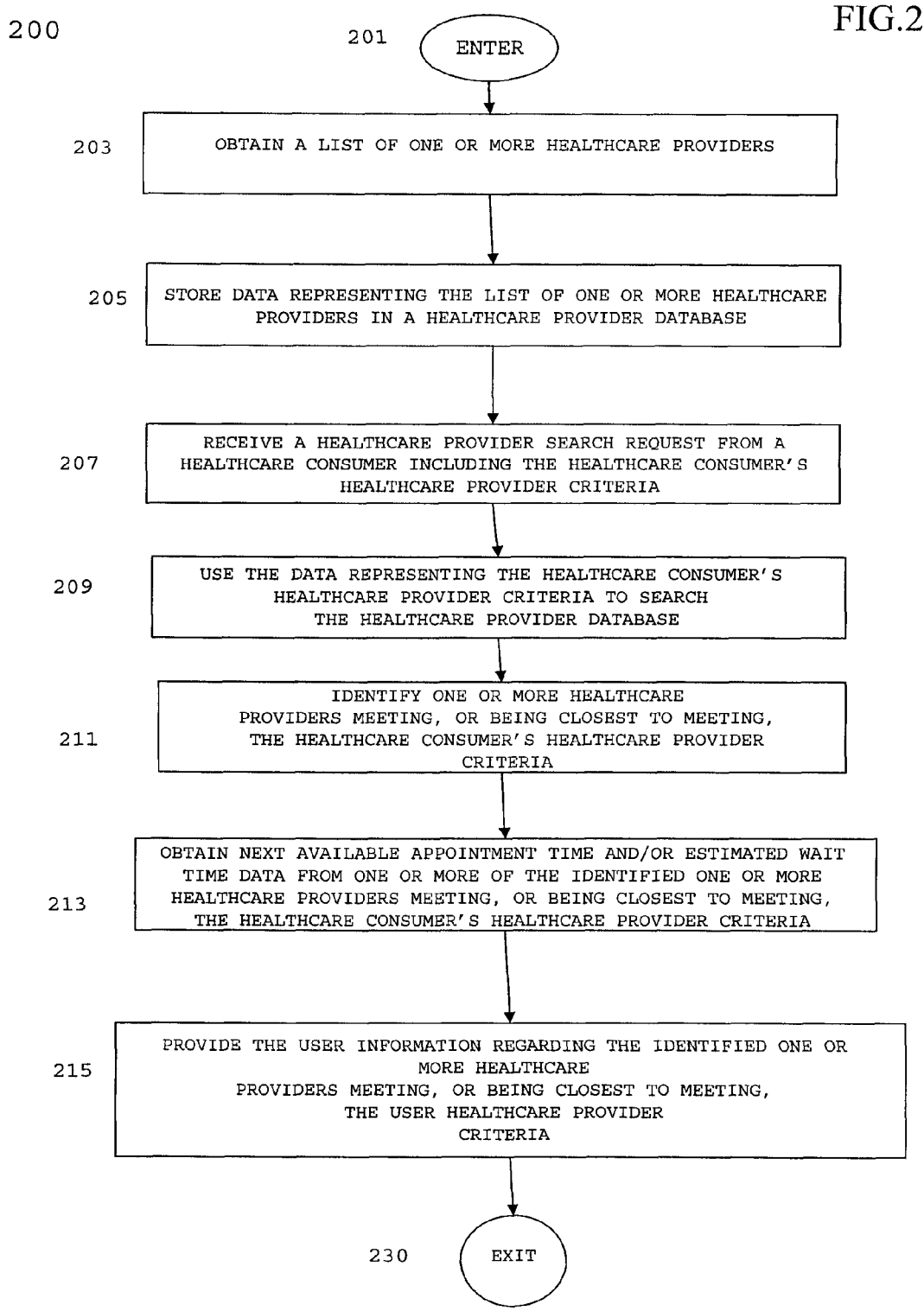
FIG. 2 is a flow chart depicting a process for selecting a healthcare provider in accordance with one embodiment.

FIG. 2 a flow chart depicting a process for selecting a healthcare provider 200 in accordance with one embodiment. Process for selecting a healthcare provider 200 begins at ENTER OPERATION 201 of FIG. 2 and process flow proceeds to OBTAIN A LIST OF ONE OR MORE HEALTHCARE PROVIDERS OPERATION 203.

In one embodiment, at OBTAIN A LIST OF ONE OR MORE HEALTHCARE PROVIDERS OPERATION 203 a healthcare provider list is obtained and/or created. In one embodiment, at OBTAIN A LIST OF ONE OR MORE HEALTHCARE PROVIDERS OPERATION 203 the healthcare provider list obtained and/or created includes various information associated with each listed healthcare provider including, but not limited to: the geographic location of the listed healthcare provider; the healthcare insurance plan networks the listed healthcare provider is associated with, and whether the listed healthcare provider is a preferred provider under various healthcare insurance plans; ratings of the listed healthcare provider from other healthcare consumers; specific capabilities and/or specialties of the listed healthcare provider such as, for example, a specific healthcare specialty and/or credential, the ability to perform blood analysis on-site, or MRI/CT imaging on site, etc.; and/or any other desired and available healthcare provider related information.

In one embodiment, at OBTAIN A LIST OF ONE OR MORE HEALTHCARE PROVIDERS OPERATION 203 all, or part, of the list of healthcare providers and associated healthcare provider information, and/or data representing the list of healthcare providers and/or associated information, includes, and/or is based on, information obtained by process for selecting a healthcare provider 200 by healthcare consumer input into a computing system, such as computing systems 100 and/or 150 of FIG. 1, through a healthcare consumer interface device, such as a keyboard, mouse, touch pad, voice recognition software, or any other means and/or mechanism for converting healthcare consumer actions into computing system processes and/or otherwise entering data into a computing system implementing at least part of process for selecting a healthcare provider 200.

In one embodiment, at OBTAIN A LIST OF ONE OR MORE HEALTHCARE PROVIDERS OPERATION 203 all, or part, of the list of healthcare providers and associated healthcare provider information, and/or data representing the list of healthcare providers and/or associated information, includes, and/or is based on, information obtained by process for selecting a healthcare provider 200 from one or more healthcare insurance plan and/or healthcare program sources such as, but not limited to: web-sites; databases associated with and/or controlled by the healthcare insurance plan and/or healthcare program; computer program products available from the healthcare insurance plan and/or healthcare program; or various other healthcare insurance plan and/or healthcare program sources. In one embodiment, the information obtained from one or more healthcare insurance plan and/or healthcare program sources includes listings of "in-network" and/or preferred providers and/or ratings of healthcare providers supplied by other plan participants and/or the healthcare insurance plan and/or healthcare program provider.

Returning to FIG. 2, at OBTAIN A LIST OF ONE OR MORE HEALTHCARE PROVIDERS OPERATION 203 all, or part, of the list of healthcare providers and associated healthcare provider information, and/or data representing the list of healthcare providers and/or associated information, includes, and/or is based on, information obtained by process for selecting a healthcare provider 200 from, or through, a computing system implemented data management system, program, package or application, such as computing system implemented data management system 180 of FIG. 1, that is a parent system for, in communication with, or is associated with, process for selecting a healthcare provider 200 (FIG. 2). In one embodiment, the computing system implemented data management system can be, but is not limited to, a personal healthcare management, personal financial, business financial, accounting, or tax preparation data management system, program, package or application that implements, includes, is accessed by, and/or is otherwise associated with, process for selecting a healthcare provider 200. In one embodiment, all, or part, of the list of healthcare providers and/or data representing the list of healthcare providers is then accessed by, and/or provided to, process for selecting a healthcare provider 200 by, and/or though, the computing system implemented data management system.

In one embodiment, at OBTAIN A LIST OF ONE OR MORE HEALTHCARE PROVIDERS OPERATION 203 all, or part, of the list of healthcare providers and associated healthcare provider information, and/or data representing the list of healthcare providers and/or associated information, includes, and/or is based on, information obtained by process for selecting a healthcare provider 200 from web-sites and/or display screens using screen scraping technology, and/or any similar data gathering technology, whether known at the time of filing or as developed thereafter.

In one embodiment, at OBTAIN A LIST OF ONE OR MORE HEALTHCARE PROVIDERS OPERATION 203 all, or part, of the list of healthcare providers and associated healthcare provider information, and/or data representing the list of healthcare providers and/or associated information, includes, and/or is based on, information obtained by process for selecting a healthcare provider 200 from any combination of the above sources and/or from any other source of healthcare providers, healthcare provider information, and/or data representing healthcare providers whether known at the time of filing or as developed thereafter.

In one embodiment, once a healthcare provider list is obtained and/or created at OBTAIN A LIST OF ONE OR MORE HEALTHCARE PROVIDERS OPERATION 203, the healthcare provider list and associated healthcare provider information is updated periodically on scheduled intervals, as the data changes, or in both instances.

In one embodiment, once a healthcare provider list is obtained and/or created at OBTAIN A LIST OF ONE OR MORE HEALTHCARE PROVIDERS OPERATION 203 process flow proceeds to STORE DATA REPRESENTING THE LIST OF ONE OR MORE HEALTHCARE PROVIDERS IN A HEALTHCARE PROVIDER DATABASE OPERATION 205.

In one embodiment, at STORE DATA REPRESENTING THE LIST OF ONE OR MORE HEALTHCARE PROVIDERS IN A HEALTHCARE PROVIDER DATABASE OPERATION 205 data representing the healthcare provider list and/or associated healthcare provider information is stored in a healthcare provider database that is local, remote, or a combination of local and remote.

In one embodiment, the healthcare provider database of STORE DATA REPRESENTING THE LIST OF ONE OR MORE HEALTHCARE PROVIDERS IN A HEALTHCARE PROVIDER DATABASE OPERATION 205 is a data storage device, such as database 170 of FIG. 1, a server system, such as server system 120 of FIG. 1, or computing system, such as computing systems 100 and/or 150 of FIG. 1, or a designated portion of one or more server systems or computing systems, or a distributed database, or an external and/or portable hard drive, or any combination thereof, that is local, remote, or a combination of local and remote. Returning to FIG. 2, in one embodiment, the healthcare provider database of STORE DATA REPRESENTING THE LIST OF ONE OR MORE HEALTHCARE PROVIDERS IN A HEALTHCARE PROVIDER DATABASE OPERATION 205 is a dedicated mass storage device implemented in software, hardware, or a combination of hardware and software. In one embodiment, the healthcare provider database of STORE DATA REPRESENTING THE LIST OF ONE OR MORE HEALTHCARE PROVIDERS IN A HEALTHCARE PROVIDER DATABASE OPERATION 205 includes a web-based function accessible through a private and/or public network.

In one embodiment, the healthcare provider database of STORE DATA REPRESENTING THE LIST OF ONE OR MORE HEALTHCARE PROVIDERS IN A HEALTHCARE PROVIDER DATABASE OPERATION 205 is accessible through a private and/or public network, such as network 130 of FIG. 1, and/or an Internet connection. As noted above, network 130 can be a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

In one embodiment, the healthcare provider database of STORE DATA REPRESENTING THE LIST OF ONE OR MORE HEALTHCARE PROVIDERS IN A HEALTHCARE PROVIDER DATABASE OPERATION 205 is accessible using a computing system such as a desktop computer, a laptop computer, a hand held computer, any portable computer, a workstation, a two-way pager, a cellular telephone, a smart phone, a digital wireless telephone, a Personal Digital Assistant (PDA), a server computer, an Internet appliance, or any other device, or any desired combination of these devices.

As noted above, in one embodiment, once a healthcare provider list is obtained and/or created at OBTAIN A LIST OF ONE OR MORE HEALTHCARE PROVIDERS OPERATION 203, the healthcare provider list and associated healthcare provider information is updated periodically on scheduled intervals, as the data changes, or in both instances. In addition, in one embodiment, the data in the healthcare provider database of STORE DATA REPRESENTING THE LIST OF ONE OR MORE HEALTHCARE PROVIDERS IN A HEALTHCARE PROVIDER DATABASE OPERATION 205 is also updated on a periodic basis, as the data changes, or in both instances.

In one embodiment, once data representing the healthcare provider list, and/or associated healthcare provider information is stored in a healthcare provider database at STORE DATA REPRESENTING THE LIST OF ONE OR MORE HEALTHCARE PROVIDERS IN A HEALTHCARE PROVIDER DATABASE OPERATION 205, process flow proceeds to RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207.

In one embodiment, at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 a healthcare consumer initiates a healthcare provider search request. In one embodiment, the healthcare provider search request includes one or more healthcare consumer criteria for acceptable/desired healthcare providers and/or healthcare services needed.

In one embodiment, at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207, the healthcare consumer initiates a healthcare provider search request using a computing system. As noted above, herein a computing system can be a desktop computer, a portable computer, a workstation, a two-way pager, a cellular telephone, a smart phone, a digital wireless telephone, a PDA, a server computer, an Internet appliance, or any other device that includes components that can execute all, or part, of process for selecting a healthcare provider 200, and/or a computing system implemented data management system, and/or a global positioning satellite capability, in accordance with at least one of the embodiments as described herein. Similarly, a computing system may be comprised of multiple different computers, wireless devices, cellular telephones, digital telephones, two-way pagers, personal digital assistants, server computers, or any desired combination of these devices, that are coupled to perform the processes and/or operations as described herein.

In one embodiment, at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207, the healthcare consumer initiates a healthcare provider search request via a mobile computing system which includes all or part of the data representing the healthcare provider list of STORE DATA REPRESENTING THE LIST OF ONE OR MORE HEALTHCARE PROVIDERS IN A HEALTHCARE PROVIDER DATABASE OPERATION 205.

In one embodiment, at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207, the healthcare consumer initiates a healthcare provider search request via connection to a network, such as network 130 of FIG. 1. As noted above, in one embodiment, network 130 can be any network or network system that is of interest to a healthcare consumer such as, a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

As noted above, in one embodiment, at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207, the healthcare provider search request initiated by the consumer includes one or more healthcare consumer criteria for acceptable/desired healthcare providers and/or healthcare services needed.

In one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, any healthcare consumer provided parameters/criteria. For example, in one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, a healthcare provider being closest to the healthcare consumer in terms of distance from the healthcare consumer's current location or a healthcare consumer designated location.

As another example, in one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, healthcare providers closest to the healthcare consumer in terms of estimated time to get to the healthcare provider at the time of the request/need. In one embodiment, this criterion could include, and be determined based on, estimated/average traffic delays and/or relatively real time traffic update data, as is available through some computing systems having a GPS capability, as discussed below, and/or various web-based functions.

As another example, in one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, healthcare providers in specific neighborhoods and/or parts of a city, or not in specific neighborhoods and/or parts of a city. In one embodiment, a healthcare consumer may limit potential healthcare providers to those in known, and/or safer, neighborhoods, as opposed to unknown, and/or less safe, neighborhoods. In one embodiment, a healthcare consumer may limit potential healthcare providers to those relatively close to a known location, place of employment, or a relative's/friend's residence or place of employment.

As another example, in one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, healthcare providers that subscribe or belong to the healthcare consumer's healthcare insurance plan network, i.e. healthcare insurance plan preferred providers, whose fees are most completely covered by the healthcare insurance plan. In one embodiment, the healthcare consumer may require that only providers within the healthcare consumer's healthcare network be searched in order to control cost and/or most efficiently utilize healthcare and/or financial resources.

As another example, in one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, healthcare providers having designated ratings from other healthcare consumers. In one embodiment, the healthcare consumer may restrict potential healthcare providers to those having a specific rating/satisfaction level from other healthcare consumers.

As another example, in one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, healthcare providers that have specific capabilities such as, for example, specific credentials and or service certifications, the ability to perform blood analysis on-site, or MRI/CT imaging on site. Likewise, in one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, a specific healthcare service needed/desired by the healthcare consumer.

In one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, any other healthcare consumer criteria and/or combination of the healthcare consumer criteria.

In one embodiment, the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 are prioritized by the healthcare consumer. For instance, as a specific example, in one embodiment, in a non-emergency situation, a healthcare consumer may dictate that a healthcare provider being in the healthcare consumer's healthcare insurance plan network, i.e., being an "in-network" provider, is most important or first priority. Then priority two may be to find the closest "in-network" healthcare provider in terms of distance. Priority three might be that the healthcare provider be in a specific part of town. As another example, in an emergency situation, a healthcare consumer may have closest provider, in terms of time or distance, as the first priority criterion, and perhaps the only criterion.

In one embodiment, pre-defined sets of prioritized healthcare consumer criteria are created for various scenarios such that specific prioritized criteria are implemented automatically by a healthcare consumer identifying the type of healthcare issue. Again, using the examples above, in one embodiment, a healthcare consumer has a pre-defined non-emergency set of prioritized criteria such as a healthcare provider being in the healthcare consumer's healthcare insurance plan network being most important, i.e., priority one. Then priority two as the closest healthcare provider in terms of distance, and then priority three being that the healthcare provider is in a specific part of town. In contrast, in one embodiment, a healthcare consumer has a pre-defined emergency set of prioritized criteria that dictate that the closest provider in terms of time, or distance, is the priority one criterion, and perhaps the only criterion. In one embodiment, a healthcare consumer has a pre-defined healthcare issue related sets of prioritized criteria. For instance a diabetic healthcare consumer may pre-define insulin shock related sets of prioritized criteria.

In one embodiment, at least part of the healthcare consumer's healthcare provider criteria is obtained by process for selecting a healthcare provider at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 by healthcare consumer input into a computing system, such as computing system 100 and/or 150 of FIG. 1, through a healthcare consumer interface device, such as a keyboard, mouse, touch pad, voice recognition software, or any other means and/or mechanism for converting healthcare consumer actions into computing system processes and/or otherwise entering data into a computing system implementing at least part of process for selecting a healthcare provider 200 (FIG. 2).

In one embodiment, all, or part of, the healthcare consumer's healthcare provider criteria is obtained at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 from, or through, one or more healthcare insurance plan sources such as, but not limited to: web-sites; databases associated with and/or controlled by the healthcare insurance plan; computer program products available from the healthcare insurance plan; or various other healthcare insurance plan sources.

In one embodiment, all, or part of, the healthcare consumer's healthcare provider criteria is obtained at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 from, or through, a computing system implemented data management system, program, package or application that is a parent system for, and/or is associated with, process for selecting a healthcare provider 200. In some embodiments, all, or part of, the healthcare consumer's healthcare provider criteria is then accessed by, and/or provided to, process for selecting a healthcare provider 200 by, and/or though, the computing system implemented data management system.

In one embodiment, at least part of the healthcare consumer's healthcare provider criteria obtained at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes, and/or is based on, information obtained from web-sites and/or display screens using screen scraping, or similar data gathering, technology.

In some embodiments, all, or part, of the healthcare consumer's healthcare provider criteria is obtained at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 by process for selecting a healthcare provider 200 from any combination of the above sources and/or from any other source of healthcare consumer criteria data, whether known at the time of filing or as developed thereafter.

As discussed above, in one embodiment, the healthcare consumer's healthcare provider criteria obtained at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 includes healthcare provider criteria based on the position of the healthcare provider relative to a given location, such as the healthcare consumer's present location. In one embodiment, a healthcare consumer's present location is obtained by process for selecting a healthcare provider 200 by healthcare consumer input into a computing system through a healthcare consumer interface device, such as a keyboard, mouse, touch pad, voice recognition software, or any other means and/or mechanism for converting healthcare consumer actions into computing system processes and/or otherwise entering data into a computing system implementing at least part of process for selecting a healthcare provider 200. In one embodiment, the computing system is a desktop computer, a laptop computer, a hand held computer, any portable computer, a workstation, a two-way pager, a cellular telephone, a smart phone, a digital wireless telephone, a Personal Digital Assistant (PDA), a server computer, an Internet appliance, a GPS device, or any other device, or any desired combination of these devices.

In one embodiment, a healthcare consumer's present location is provided by a computing system having a global positioning satellite capability. In one embodiment, the computing system having a global positioning satellite capability is a portable, and/or handheld, and/or vehicle mounted, global positioning satellite device. In one embodiment the computing system having a global positioning satellite capability is a desktop computer, a laptop computer, a hand held computer, any portable computer, a workstation, a two-way pager, a cellular telephone, a smart phone, a digital wireless telephone, a Personal Digital Assistant (PDA), a server computer, an Internet appliance, or any other device, or any desired combination of these devices, that includes a global positioning satellite capability.

In one embodiment, once a healthcare consumer initiates a healthcare provider search request and/or provides one or more healthcare consumer criteria for acceptable/desired healthcare providers and/or healthcare services needed at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207, process flow proceeds to USE THE DATA REPRESENTING THE HEALTHCARE CONSUMER'S HEALTHCARE PROVIDER CRITERIA TO SEARCH THE HEALTHCARE PROVIDER DATABASE OPERATION 209.

In one embodiment, at USE THE DATA REPRESENTING THE HEALTHCARE CONSUMER'S HEALTHCARE PROVIDER CRITERIA TO SEARCH THE HEALTHCARE PROVIDER DATABASE OPERATION 209 the data representing the healthcare provider search request, and/or one or more healthcare consumer criteria for acceptable/desired healthcare providers, and/or healthcare services needed, of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207, is used to search the healthcare provider database of STORE DATA REPRESENTING THE LIST OF ONE OR MORE HEALTHCARE PROVIDERS IN A HEALTHCARE PROVIDER DATABASE OPERATION 205 to try and identify one or more healthcare providers most closely meeting the healthcare consumer's criteria at the time of the healthcare provider search request.

In one embodiment, at USE THE DATA REPRESENTING THE HEALTHCARE CONSUMER'S HEALTHCARE PROVIDER CRITERIA TO SEARCH THE HEALTHCARE PROVIDER DATABASE OPERATION 209 the healthcare consumer, and/or a designated representative of the healthcare consumer, is provided access to at least part of the data in the healthcare provider database of STORE DATA REPRESENTING THE LIST OF ONE OR MORE HEALTHCARE PROVIDERS IN A HEALTHCARE PROVIDER DATABASE OPERATION 205.

In one embodiment, at USE THE DATA REPRESENTING THE HEALTHCARE CONSUMER'S HEALTHCARE PROVIDER CRITERIA TO SEARCH THE HEALTHCARE PROVIDER DATABASE OPERATION 209 the healthcare consumer, and/or a designated representative of the healthcare consumer, is provided access to at least part of the data in the healthcare provider database of STORE DATA REPRESENTING THE LIST OF ONE OR MORE HEALTHCARE PROVIDERS IN A HEALTHCARE PROVIDER DATABASE OPERATION 205 through a private and/or public network and/or Internet connection, such as network 130 of FIG. 1. As noted above, network 130 can be a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems, whether available or known at the time of filing or as later developed.

In one embodiment, at USE THE DATA REPRESENTING THE HEALTHCARE CONSUMER'S HEALTHCARE PROVIDER CRITERIA TO SEARCH THE HEALTHCARE PROVIDER DATABASE OPERATION 209 the healthcare consumer, and/or a designated representative of the healthcare consumer, is provided access to at least part of the data in the healthcare provider database of STORE DATA REPRESENTING THE LIST OF ONE OR MORE HEALTHCARE PROVIDERS IN A HEALTHCARE PROVIDER DATABASE OPERATION 205 using a computing system such as a desktop computer, a laptop computer, a hand held computer, any portable computer, a workstation, a two-way pager, a cellular telephone, a smart phone, a digital wireless telephone, a Personal Digital Assistant (PDA), a server computer, an Internet appliance, or any other device, or any desired combination of these devices.

In one embodiment, at USE THE DATA REPRESENTING THE HEALTHCARE CONSUMER'S HEALTHCARE PROVIDER CRITERIA TO SEARCH THE HEALTH- CARE PROVIDER DATABASE OPERATION 209 the healthcare consumer, and/or a designated representative of the healthcare consumer, is provided access to at least part of the data in the healthcare provider database of STORE DATA REPRESENTING THE LIST OF ONE OR MORE HEALTHCARE PROVIDERS IN A HEALTHCARE PROVIDER DATABASE OPERATION 205 using any means, method, mechanism, procedure, product, or process for accessing data, such as the healthcare provider lists and related information data of OBTAIN A LIST OF ONE OR MORE HEALTHCARE PROVIDERS OPERATION 203, stored in a database, such as the healthcare provider database of STORE DATA REPRESENTING THE LIST OF ONE OR MORE HEALTHCARE PROVIDERS IN A HEALTHCARE PROVIDER DATABASE OPERATION 205, whether known at the time of filing or as developed thereafter.

In one embodiment, once the healthcare consumer, and/or a designated representative of the healthcare consumer, is provided access to at least part of the data in the healthcare provider database of STORE DATA REPRESENTING THE LIST OF ONE OR MORE HEALTHCARE PROVIDERS IN A HEALTHCARE PROVIDER DATABASE OPERATION 205 at USE THE DATA REPRESENTING THE HEALTHCARE CONSUMER'S HEALTHCARE PROVIDER CRITERIA TO SEARCH THE HEALTHCARE PROVIDER DATABASE OPERATION 209, data representing the healthcare consumer's healthcare provider criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 is used to search the healthcare provider database to identify healthcare providers most closely meeting the healthcare consumer's criteria at the time of the search request/need.

In one embodiment, the healthcare consumer's healthcare provider criteria data is made available to search the healthcare provider database at USE THE DATA REPRESENTING THE HEALTHCARE CONSUMER'S HEALTHCARE PROVIDER CRITERIA TO SEARCH THE HEALTHCARE PROVIDER DATABASE OPERATION 209 via data transfer from any computing system, such as those discussed herein, known in the art at the time of filing, or as developed thereafter, capable of transmitting data. In one embodiment, the healthcare consumer's healthcare provider criteria data is made available to search the healthcare provider database at USE THE DATA REPRESENTING THE HEALTHCARE CONSUMER'S HEALTHCARE PROVIDER CRITERIA TO SEARCH THE HEALTHCARE PROVIDER DATABASE OPERATION 209 via a network or network system such as those discussed herein, known in the art at the time of filing, or as developed thereafter.

In one embodiment, the healthcare consumer's healthcare provider criteria data is made available to search the healthcare provider database at USE THE DATA REPRESENTING THE HEALTHCARE CONSUMER'S HEALTHCARE PROVIDER CRITERIA TO SEARCH THE HEALTHCARE PROVIDER DATABASE OPERATION 209 by storing the healthcare consumer's healthcare provider criteria data on a healthcare consumer's healthcare provider criteria database and then providing for communication and/or data transfer between the healthcare consumer's healthcare provider criteria database and the healthcare provider database of STORE DATA REPRESENTING THE LIST OF ONE OR MORE HEALTHCARE PROVIDERS IN A HEALTHCARE PROVIDER DATABASE OPERATION 205 at the time of the search request of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207. In one embodiment, the healthcare consumer's healthcare provider criteria database is a data storage device, a designated server system or computing system, or a designated portion of one or more server systems or computing systems, or a distributed database, or an external and/or portable hard drive. In one embodiment, the healthcare consumer's healthcare provider criteria database is a dedicated mass storage device implemented in software, hardware, or a combination of hardware and software. In one embodiment, the healthcare consumer's healthcare provider criteria database is a web-based function.

In one embodiment, the healthcare consumer's healthcare provider criteria is made available to search the healthcare provider database at USE THE DATA REPRESENTING THE HEALTHCARE CONSUMER'S HEALTHCARE PROVIDER CRITERIA TO SEARCH THE HEALTHCARE PROVIDER DATABASE OPERATION 209 via a computer program product as defined herein, such as, but not limited to, a data storage disk or memory stick, and providing.

In one embodiment, once the healthcare consumer, and/or a designated representative of the healthcare consumer, is provided access to at least part of the data in the healthcare provider and the data representing the healthcare provider search request, and/or one or more healthcare consumer criteria for acceptable/desired healthcare providers, and/or healthcare services needed is made available to search the healthcare provider database, the data representing the healthcare provider search request, and/or one or more healthcare consumer criteria for acceptable/desired healthcare providers and/or healthcare services needed is used to search the healthcare provider database to identify healthcare providers most closely meeting the healthcare consumer's healthcare provider criteria by any one or more search methods known in the art at the time of filing, or as developed thereafter.

For instance, in one embodiment, at USE THE DATA REPRESENTING THE HEALTHCARE CONSUMER'S HEALTHCARE PROVIDER CRITERIA TO SEARCH THE HEALTHCARE PROVIDER DATABASE OPERATION 209 the search performed is a keyword search. In one embodiment, at USE THE DATA REPRESENTING THE HEALTHCARE CONSUMER'S HEALTHCARE PROVIDER CRITERIA TO SEARCH THE HEALTHCARE PROVIDER DATABASE OPERATION 209 the search performed is a best match search or a full/exact match search.

As noted above, in one embodiment, the healthcare consumer's healthcare provider criteria are prioritized by the healthcare consumer. As also noted above, in one embodiment, pre-defined sets of prioritized healthcare consumer criteria are created for various scenarios such that specific prioritized criteria are implemented automatically by a healthcare consumer identifying the type of healthcare issue.

In these instances, at USE THE DATA REPRESENTING THE HEALTHCARE CONSUMER'S HEALTHCARE PROVIDER CRITERIA TO SEARCH THE HEALTHCARE PROVIDER DATABASE OPERATION 209 the data representing the one or more healthcare consumer criteria of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207 is used to search the healthcare provider database of STORE DATA REPRESENTING THE LIST OF ONE OR MORE HEALTHCARE PROVIDERS IN A HEALTHCARE PROVIDER DATABASE OPERATION 205 to identify and prioritize healthcare providers most closely meeting the prioritized healthcare consumer healthcare provider criteria, and/or that are on the healthcare consumer's preferred healthcare provider list, at the time of the search request/need.

Numerous means, methods, mechanism, processes and procedures are well known in the art for performing data analysis and/or searches such as the search performed at USE THE DATA REPRESENTING THE HEALTHCARE CONSUMER'S HEALTHCARE PROVIDER CRITERIA TO SEARCH THE HEALTHCARE PROVIDER DATABASE OPERATION 209. Consequently, a more detailed discussion of any specific means, methods, mechanism, processes and procedures for performing data analysis and/or searches such as the search performed at USE THE DATA REPRESENTING THE HEALTHCARE CONSUMER'S HEALTHCARE PROVIDER CRITERIA TO SEARCH THE HEALTHCARE PROVIDER DATABASE OPERATION 209 is omitted here to avoid detracting from the invention.

In one embodiment, once the data representing the healthcare provider search request, and/or one or more healthcare consumer criteria for acceptable/desired healthcare providers, and/or healthcare services needed, of RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207, is used to search the healthcare provider database to try and identify one or more healthcare providers most closely meeting the healthcare consumer's criteria at the time of the healthcare provider search request at USE THE DATA REPRESENTING THE HEALTHCARE CONSUMER'S HEALTHCARE PROVIDER CRITERIA TO SEARCH THE HEALTHCARE PROVIDER DATABASE OPERATION 209, process flow proceeds to IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211.

In one embodiment, at IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211 one or more healthcare providers are identified that most closely meet the healthcare consumer's criteria as a result of the search of the healthcare provider database of STORE DATA REPRESENTING THE LIST OF ONE OR MORE HEALTHCARE PROVIDERS IN A HEALTHCARE PROVIDER DATABASE OPERATION 205 at USE THE DATA REPRESENTING THE HEALTHCARE CONSUMER'S HEALTHCARE PROVIDER CRITERIA TO SEARCH THE HEALTHCARE PROVIDER DATABASE OPERATION 209.

In one embodiment, once one or more healthcare providers are identified that most closely meet the healthcare consumer's criteria at IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211, process flow proceeds to OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213.

In one embodiment, at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213 the availability of appointments and/or estimated wait times for one or more of the one or more healthcare providers most closely meeting the healthcare consumer's criteria at the time of the request of IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211 are obtained.

In one embodiment, at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213 the availability of appointments and/or estimated wait times for one or more of the one or more healthcare providers most closely meeting the healthcare consumer's criteria at the time of the healthcare provider search request is obtained from the one or more healthcare providers meeting, or most closely meeting, the healthcare consumer's criteria by the healthcare provider's offices/employees entering data indicating next available appointments and/or estimated delay times into an interface and/or computing system associated with, and/or accessible by, process for selecting a healthcare provider 200.

In one embodiment, at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213 the availability of appointments and/or estimated wait times for one or more of the one or more healthcare providers most closely meeting the healthcare consumer's criteria at the time of the healthcare provider search request is obtained from the one or more healthcare providers meeting, or most closely meeting, the healthcare consumer's criteria by the healthcare provider's offices/employees entering data indicating next available appointments and/or estimated delay times into an interface provided by a computing system implemented data management system, such as computing system implemented data management system 180 of FIG. 1, associated with process for selecting a healthcare provider 200 on a computing system associated with and/or implementing all, or part, of process for selecting a healthcare provider 200 and/or the computing system implemented data management system.

In one embodiment, at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213 the availability of appointments and/or estimated wait times for one or more of the one or more healthcare providers most closely meeting the healthcare consumer's criteria at the time of the healthcare provider search request is obtained from the one or more healthcare providers meeting, or most closely meeting, the healthcare consumer's criteria by the healthcare provider's offices/employees entering data indicating next available appointments and/or estimated wait times into an interface provided by a computing system implemented application, such as computing system implemented application 190 of FIG. 1, and then allowing a computing system implemented data management system associated with process for selecting a healthcare provider 200, and/or process for selecting a healthcare provider 200, and/or a computing system implemented application associated with process for selecting a healthcare provider 200, access to the computing system implemented application data.

In one embodiment, the next available appointment and/or estimated wait time data for a given healthcare provider is entered into an interface associated with a computing system implemented data management system that is associated with process for selecting a healthcare provider 200, and/or process for selecting a healthcare provider 200, and/or the computing system implemented application, manually by one or more healthcare provider personal through the interface display using an interface device.

In one embodiment, the next available appointment and/or estimated wait time data for a given healthcare provider is manually, semi-automatically, or automatically entered/determined by a computing system implemented data management system associated with process for selecting a healthcare provider 200, and/or process for selecting a healthcare provider 200, and/or the computing system implemented application, based on one or more actions taken by one or more healthcare provider personal, and/or a healthcare provider computing system, and/or a healthcare provider computing system implemented application.

For instance, in one embodiment, to determine the next available appointment for a given healthcare provider, access to a healthcare provider's computing system implemented application such as, but not limited to: a computing system implemented calendar application used by a healthcare provider; a computing system implemented patient appointment scheduling application used by a healthcare provider; a computing system implemented timer application used by a healthcare provider; a computing system implemented data processing application used by a healthcare provider; a computing system implemented healthcare record data processing application used by a healthcare provider; and/or any other a computing system implemented application used by any user is manually, semi-automatically, or automatically provided to a computing system implemented data management system associated with process for selecting a healthcare provider 200, and/or process for selecting a healthcare provider 200, to determine the next available reappointment time. In addition, in one embodiment, the appointment availability data provided to computing system implemented data management system associated with process for selecting a healthcare provider 200, and/or process for selecting a healthcare provider 200, is automatically updated at regularly scheduled intervals, when the data changes, such as an appointment cancellation, or is provided in relative real-time at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213.

As another example, to determine estimated wait time data for a given healthcare provider data entries are made, manually, semi-automatically, or automatically, at various stages of a healthcare consumer's visit to a healthcare provider, such waiting room, taking of preliminary background readings, nurse consultation, and doctor consultation. Then, in one embodiment, the time between a scheduled appointment for a healthcare consumer and the time at which the healthcare consumer actually gets to one of these stages is to determine an estimated wait time/delay time.

As another example, to determine estimated wait time data for a given healthcare provider, notice is provided, manually, semi-automatically, or automatically, when a healthcare consumer's health record maintained by the healthcare provider is accessed, in one embodiment indicating that the healthcare consumer's visit has begun. Then, in one embodiment, the time between a scheduled appointment for a healthcare consumer and the time at which the healthcare consumer's health record is accessed to determine an estimated wait time/delay time.

In various embodiments, numerous data points, whether obtained manually, semi-automatically, or automatically, are possible indicators of what stage of a visitation a given healthcare consumer is currently taking part in. Using any desired one or more of these data points, a determination can be made manually, semi-automatically, or automatically, as to any time lag, i.e., wait time, between when a healthcare consumer was scheduled to be seen and when he or she is actually being seen. Then, in one embodiment, this determined wait time is provided to process for selecting a healthcare provider 200 at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213.

In one embodiment, at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213 the availability of appointments and/or estimated wait times for one or more of the one or more healthcare providers most closely meeting the healthcare consumer's criteria at the time of the healthcare provider search request is obtained from the one or more healthcare providers meeting, or most closely meeting, the healthcare consumer's criteria by any means, mechanism, program, process, application or device capable of providing all, or part of, data indicating the availability of appointments and/or estimated wait times for one or more of the one or more healthcare providers, whether known at the time of filing or as developed thereafter.

In one embodiment, at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213 the next available appointment and/or estimated wait time data for a given healthcare provider is either transferred to process for selecting a healthcare provider 200, or is transferred to a data source accessible by process for selecting a healthcare provider 200.

In one embodiment, at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213 the next available appointment and/or estimated wait time data for a given healthcare provider is accessed by the process for selecting a healthcare provider on a computing system and/or database under the control of the healthcare provider.

In one embodiment, at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213 the next available appointment and/or estimated wait time data for a given healthcare provider is provided to process for selecting a healthcare provider 200 via any means, mechanism, method, process, procedure, or device for providing, transferring and/or accessing data, whether known at the time of filing or as developed thereafter.

In one embodiment, once the availability of appointments and/or estimated wait times for one or more of the one or more healthcare providers most closely meeting the healthcare consumer's criteria at the time of the request of IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211 are obtained at OBTAIN NEXT AVAILABLE APPOINTMENT TIME AND/OR ESTIMATED WAIT TIME DATA FROM ONE OR MORE OF THE IDENTIFIED ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 213, process flow proceeds to PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the healthcare consumer is provided information regarding one or more identified healthcare providers meeting, or coming closest to meeting, the healthcare consumer's healthcare provider criteria, along with the available appointment data and/or estimated office wait time data for the one or more identified healthcare providers.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the information identifying and/or regarding the one or more healthcare providers that most closely meet the healthcare consumer's criteria includes, but is not limited to: directions to, and/or contact information for, the one or more healthcare providers most closely meeting the healthcare consumer's healthcare provider criteria of IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211; available appointments for the one or more healthcare providers most closely meeting the healthcare consumer's healthcare provider criteria of IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211; the estimated wait time for the one or more healthcare providers most closely meeting the healthcare consumer's healthcare provider criteria of IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211; the status of the one or more healthcare providers most closely meeting the healthcare consumer's healthcare provider criteria of IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211 as either in or out of the healthcare consumer's healthcare provider network; and/or any other information identifying and/or regarding the one or more healthcare providers that most closely meet the healthcare consumer's criteria of IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the one or more healthcare providers identified at IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211 are provided to the healthcare consumer in a listing showing the next available appointment and/or the estimated wait time for each of the one or more healthcare providers.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the one or more healthcare providers identified at IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211 are provided to the healthcare consumer in a listing showing how closely they meet the healthcare consumer's criteria.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the one or more healthcare providers identified at IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211 are provided to the healthcare consumer in a listing according to specific criteria as prioritized by the healthcare consumer at RECEIVE A HEALTHCARE PROVIDER SEARCH REQUEST FROM A HEALTHCARE CONSUMER INCLUDING THE HEALTHCARE CONSUMER'S HEALTHCARE PROVIDER CRITERIA OPERATION 207.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the one or more healthcare providers identified at IDENTIFY ONE OR MORE HEALTHCARE PROVIDERS MEETING, OR BEING CLOSEST TO MEETING, THE HEALTHCARE CONSUMER'S HEALTHCARE PROVIDER CRITERIA OPERATION 211 are provided to the healthcare consumer in a listing based on any display rules desired.

In one embodiment, information regarding one or more identified healthcare providers meeting, or coming closest to meeting, the healthcare consumer's healthcare provider criteria, along with the available appointment data and/or estimated office wait time data for the one or more identified healthcare providers is provided to the healthcare consumer at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 via data transfer to a computing system such as a desktop computer, a laptop computer, a hand held computer, any portable computer, a workstation, a two-way pager, a cellular telephone, a smart phone, a digital wireless telephone, a PDA, a server computer, an Internet appliance, a GPS device, or any other device, or any desired combination of these devices, capable of transmitting/displaying data.

In one embodiment, information regarding one or more identified healthcare providers meeting, or coming closest to meeting, the healthcare consumer's healthcare provider criteria, along with the available appointment data and/or estimated office wait time data for the one or more identified healthcare providers is provided to the healthcare consumer at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 via a network or network system such as, a peer-to-peer network, a hybrid peer-to-peer network, a Local Area Network (LAN), a Wide Area Network (WAN), a public network, such as the Internet, a private network, a combination of different network types, or other wireless, wired, and/or a wireless and wired combination network capable of allowing communication between two or more computing systems and/or databases, whether available or known at the time of filing or as later developed.

In one embodiment, information regarding one or more identified healthcare providers meeting, or coming closest to meeting, the healthcare consumer's healthcare provider criteria, along with the available appointment data and/or estimated office wait time data for the one or more identified healthcare providers is provided to the healthcare consumer at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 by storing data representing the information on a results database and then providing the healthcare consumer access to the results database. In one embodiment, the results database is a data storage device, a designated server system or computing system, or a designated portion of one or more server systems or computing systems, or a distributed database, or an external and/or portable hard drive. In one embodiment, the results database is a dedicated mass storage device implemented in software, hardware, or a combination of hardware and software. In one embodiment, the results database is a web-based function.

In one embodiment, information regarding one or more identified healthcare providers meeting, or coming closest to meeting, the healthcare consumer's healthcare provider criteria, along with the available appointment data and/or estimated office wait time data for the one or more identified healthcare providers is provided to the healthcare consumer at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 via a computer program product as defined herein.

In one embodiment, information regarding one or more identified healthcare providers meeting, or coming closest to meeting, the healthcare consumer's healthcare provider criteria, along with the available appointment data and/or estimated office wait time data for the one or more identified healthcare providers is provided to the healthcare consumer at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 via any means, mechanism, method, process, procedure, or device for providing a healthcare consumer information and/or data, whether known at the time of filing or as developed thereafter.

In one embodiment, once information regarding one or more identified healthcare providers meeting, or coming closest to meeting, the healthcare consumer's healthcare provider criteria, along with the available appointment data and/or estimated office wait time data for the one or more identified healthcare providers is provided to the healthcare consumer at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215, the healthcare consumer is then provided the opportunity to select one of the healthcare providers meeting, or coming closest to meeting, the healthcare consumer's healthcare provider criteria.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the healthcare consumer is provided the opportunity to select and schedule a specific appointment with one of the healthcare providers.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the healthcare consumer is provided the opportunity to select a healthcare provider and the next specific appointment with that healthcare provider is automatically scheduled.

In one embodiment, at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215 the healthcare provider is automatically selected based on the healthcare provider meeting, or coming closest to meeting, the healthcare consumer's healthcare provider criteria, and/or having the soonest available appointment, and/or the shortest wait time, and the next specific appointment with that healthcare provider is automatically scheduled.

In one embodiment, once information regarding one or more identified healthcare providers meeting, or coming closest to meeting, the healthcare consumer's healthcare provider criteria, along with the available appointment data and/or estimated office wait time data for the one or more identified healthcare providers is provided to the healthcare consumer, and, in one embodiment, the healthcare consumer is provided the opportunity to select one of the healthcare providers to schedule an appointment at PROVIDE THE USER INFORMATION REGARDING THE IDENTIFIED ONE OR MORE HEALTHCARE PROVIDERS MEETING, OR BEING CLOSEST TO MEETING, THE USER HEALTHCARE PROVIDER CRITERIA OPERATION 215, process flow proceeds to EXIT OPERATION 230.

In one embodiment, at EXIT OPERATION 230 process for selecting a healthcare provider 200 is exited to await new data and/or another search request.

Using process for selecting a healthcare provider 200, a list of healthcare providers and related healthcare provider information is created and stored in a healthcare provider database. Then, when a healthcare service need arises, a healthcare consumer can use pre-defined, or currently defined, healthcare provider criteria data, and/or preferred healthcare provider list data, to search the healthcare provider database, at the time of need, to identify one or more healthcare providers meeting, or coming closest to meeting, the healthcare consumer's healthcare provider criteria in "real-time". In one embodiment, the healthcare consumer is then provided with next available appointment times and/or estimated wait times for one or more of the one or more healthcare providers meeting, or coming closest to meeting, the healthcare consumer's healthcare provider criteria. Consequently, using process for selecting a healthcare provider 200, a healthcare consumer can determine not only the closest healthcare provider in terms of time and/or distance, but also the healthcare provider that has soonest available appointment and the shortest wait time in order to choose the healthcare provider offering the quickest opportunity for the healthcare consumer to actually receive healthcare services.

As discussed in more detail above, using the above embodiments, with little or no modification and/or healthcare consumer input, there is considerable flexibility, adaptability, and opportunity for customization to meet the specific needs of various healthcare consumers under numerous circumstances.

The present invention has been described in particular detail with respect to specific possible embodiments. Those of skill in the art will appreciate that the invention may be practiced in other embodiments. For example, the nomenclature used for components, capitalization of component designations and terms, the attributes, data structures, or any other programming or structural aspect is not significant, mandatory, or limiting, and the mechanisms that implement the invention or its features can have various different names, formats, and/or protocols. Further, the system and/or functionality of the invention may be implemented via various combinations of software and hardware, as described, or entirely in hardware elements. Also, particular divisions of functionality between the various components described herein are merely exemplary, and not mandatory or significant. Consequently, functions performed by a single component may, in other embodiments, be performed by multiple components, and functions performed by multiple components may, in other embodiments, be performed by a single component.

Some portions of the above description present the features of the present invention in terms of algorithms and symbolic representations of operations, or algorithm-like representations, of operations on information/data. These algorithmic and/or algorithm-like descriptions and representations are the means used by those of skill in the art to most effectively and efficiently convey the substance of their work to others of skill in the art. These operations, while described functionally or logically, are understood to be implemented by computer programs and/or computing systems. Furthermore, it has also proven convenient at times to refer to these arrangements of operations as steps or modules or by functional names, without loss of generality.

Unless specifically stated otherwise, as would be apparent from the above discussion, it is appreciated that throughout the above description, discussions utilizing terms such as "obtaining", "receiving" "initiating", "using", "identifying", "defining", "accessing", "obtaining", "transferring", "storing", "providing", etc., refer to the action and processes of a computing system or similar electronic device that manipulates and operates on data represented as physical (electronic) quantities within the computing system memories, resisters, caches or other information storage, transmission or display devices.

Certain aspects of the present invention include process steps or operations and instructions described herein in an algorithmic and/or algorithmic-like form. It should be noted that the process steps and/or operations and instructions of the present invention can be embodied in software, firmware, and/or hardware, and when embodied in software, can be downloaded to reside on and be operated from different platforms used by real time network operating systems.

The present invention also relates to an apparatus or system for performing the operations described herein. This apparatus or system may be specifically constructed for the required purposes, or the apparatus or system can comprise a general purpose system selectively activated or configured/reconfigured by a computer program stored on a computer program product as defined herein that can be accessed by a computing system or other device.

Those of skill in the art will readily recognize that the algorithms and operations presented herein are not inherently related to any particular computing system, computer architecture, computer or industry standard, or any other specific apparatus. Various general purpose systems may also be used with programs in accordance with the teaching herein, or it may prove more convenient/efficient to construct more specialized apparatuses to perform the required operations described herein. The required structure for a variety of these systems will be apparent to those of skill in the art, along with equivalent variations. In addition, the present invention is not described with reference to any particular programming language and it is appreciated that a variety of programming languages may be used to implement the teachings of the present invention as described herein, and any references to a specific language or languages are provided for illustrative purposes only and for enablement of the contemplated most closely meeting mode of the invention at the time of filing.

The present invention is well suited to a wide variety of computer network systems operating over numerous topologies. Within this field, the configuration and management of large networks comprise storage devices and computers that are communicatively coupled to similar and/or dissimilar computers and storage devices over a private network, a LAN, a WAN, a private network, or a public network, such as the Internet.

It should also be noted that the language used in the specification has been principally selected for readability, clarity and instructional purposes, and may not have been selected to delineate or circumscribe the inventive subject matter. Accordingly, the disclosure of the present invention is intended to be illustrative, but not limiting, of the scope of the invention, which is set forth in the claims below.

In addition, the operations shown in the FIG.s are identified using a particular nomenclature for ease of description and understanding, but other nomenclature is often used in the art to identify equivalent operations.

Therefore, numerous variations, whether explicitly provided for by the specification or implied by the specification or not, may be implemented by one of skill in the art in view of this disclosure.

What is claimed is:

1. A computing system implemented process for selecting a healthcare provider comprising:

obtaining a list of one or more healthcare providers, the list of one or more healthcare providers comprising information associated with one or more healthcare providers;

initiating a healthcare provider search request using one or more healthcare consumer criteria for selecting a healthcare provider;

in response to the healthcare provider search request, searching the list of one or more healthcare providers to identify one or more healthcare providers that match at least of the healthcare consumer criteria for selecting a healthcare provider, the process operable to match criteria including one or more geographical areas to exclude from search results thus ensuring that no providers located within the excluded geographical areas are included within the identified one or more healthcare providers, the one or more geographical areas to exclude being provided in the search request;

obtaining available appointment time data and estimated wait time data from at least one of the identified one or more healthcare providers that match at least one of the healthcare consumer criteria for selecting a healthcare provider; and providing the healthcare consumer with information regarding at least one of the identified one or more healthcare providers that match at least one of the healthcare consumer criteria for selecting a healthcare provider, the information comprising appointment time data and estimated wait time data associated with the at least one of the identified one or more healthcare providers that match at least one of the healthcare consumer criteria for selecting a healthcare provider.

2. The computing system implemented process for selecting a healthcare provider of claim 1, wherein;

the data representing the list of one or more healthcare providers is stored in a healthcare provider database.

3. The computing system implemented process for selecting a healthcare provider of claim 2, wherein;

the healthcare provider database is a network-based database.

4. The computing system implemented process for selecting a healthcare provider of claim 3, wherein;

the healthcare provider database is a web-based database.

5. The computing system implemented process for selecting a healthcare provider of claim 1, wherein;

the information associated with one or more healthcare providers is selected from the group of information associated with one or more healthcare providers consisting of:

the geographic location of the healthcare provider;

healthcare insurance plans that include the healthcare provider in the healthcare insurance plan's network of healthcare providers;

services provided by the healthcare provider; or ratings of the healthcare provider.

6. The computing system implemented process for selecting a healthcare provider of claim 1, wherein;

the one or more healthcare consumer criteria for selecting a healthcare provider comprises the criterion that the healthcare provider be the healthcare provider closest to a designated location in terms of distance.

7. The computing system implemented process for selecting a healthcare provider of claim 1, wherein;

the one or more healthcare consumer criteria for selecting a healthcare provider comprises the criterion that the healthcare provider be the healthcare provider closest to a healthcare consumer's location at the approximate time of initiating the healthcare provider search request in terms of distance.

8. The computing system implemented process for selecting a healthcare provider of claim 1, wherein;

the one or more healthcare consumer criteria for selecting a healthcare provider comprises the criterion that the healthcare provider is within a designated distance of healthcare consumer's location at the approximate time of initiating the healthcare provider search request.

9. The computing system implemented process for selecting a healthcare provider of claim 1, wherein;

the one or more healthcare consumer criteria for selecting a healthcare provider comprises the criterion that the healthcare provider be the healthcare provider closest to a designated location in terms of time.

10. The computing system implemented process for selecting a healthcare provider of claim 1, wherein;

the one or more healthcare consumer criteria for selecting a healthcare provider comprises the criterion that the healthcare provider be the healthcare provider closest to the healthcare consumer's location at the approximate time of initiating the healthcare provider search request in terms of time.

11. The computing system implemented process for selecting a healthcare provider of claim 1, wherein;

the one or more healthcare consumer criteria for selecting a healthcare provider comprises the criterion that the healthcare provider be within a designated travel time of healthcare consumer's location at the approximate time of initiating the healthcare provider search request.

12. The computing system implemented process for selecting a healthcare provider of claim 1, wherein;

the one or more healthcare consumer criteria for selecting a healthcare provider comprise the criterion that the healthcare provider belongs to a designated healthcare insurance plan's network of providers.

13. The computing system implemented process for selecting a healthcare provider of claim 1, wherein;

obtaining available appointment time data and estimated wait time data from at least one of the identified one or more healthcare providers that match at least one of the healthcare consumer criteria for selecting a healthcare provider comprises obtaining available appointment time data associated with a given one of the at least one identified one or more healthcare providers that match at least one of the healthcare consumer criteria for selecting a healthcare provider from a computing system implemented application running on the given healthcare provider's computing system.

14. The computing system implemented process for selecting a healthcare provider of claim 1, wherein;

obtaining available appointment time data and estimated wait time data from at least one of the identified one or more healthcare providers that match at least one of the healthcare consumer criteria for selecting a healthcare provider comprises obtaining estimated wait time data associated with a given one of the at least one of the identified one or more healthcare providers that match at least one of the healthcare consumer criteria for selecting a healthcare provider from a computing system implemented application running on the given healthcare provider's computing system.

15. The computing system implemented process for selecting a healthcare provider of claim 14, wherein;

the estimated wait time data for the given healthcare provider is determined based on a time difference between when a designated event occurs at the healthcare provider location for a specific appointment and when the designated event should have occurred at the healthcare provider location for the specific appointment.

16. The computing system implemented process for selecting a healthcare provider of claim 1, wherein;

providing the healthcare consumer with information regarding at least one of the identified one or more healthcare providers that match at least one of the healthcare consumer criteria for selecting a healthcare provider comprises providing the healthcare consumer with information regarding at least one of the identified one or more healthcare providers that match at least one of the healthcare consumer criteria selected from the group of information associated with one or more healthcare providers consisting of:

contact information for the healthcare provider the geographic location and/or address of the healthcare provider;

healthcare insurance plans that include the healthcare provider in the healthcare insurance plan's network of healthcare providers;

services provided by the healthcare provider;

directions to healthcare provider from a designated location; or ratings of the healthcare provider.

17. The computing system implemented process for selecting a healthcare provider of claim 1, further comprising:

providing the healthcare consumer with the capability to make a selected appointment with a selected one of the at least one of the identified one or more healthcare providers that match at least one of the healthcare consumer criteria for selecting a healthcare provider.

18. A computer program product for selecting a healthcare provider comprising:

a nontransitory computer readable medium;

and computer program code, encoded on the computer readable medium, comprising computer readable instructions for:

obtaining a list of one or more healthcare providers, the list of one or more healthcare providers comprising information associated with one or more healthcare providers;

initiating a healthcare provider search request using one or more healthcare consumer criteria for selecting a healthcare provider;

in response to the healthcare provider search request, searching the list of one or more healthcare providers to identify one or more healthcare providers that match at least of the healthcare consumer criteria for selecting a healthcare provider, the process operable to match criteria including one or more geographical areas to exclude from search results thus ensuring that no providers located within the excluded geographical areas are included within the identified one or more healthcare providers, the one or more geographical areas to exclude being provided in the search request;

obtaining available appointment time data and estimated wait time data from at least one of the identified one or more healthcare providers that match at least one of the healthcare consumer criteria for selecting a healthcare provider; and providing the healthcare consumer with information regarding at least one of the identified one or more healthcare providers that match at least one of the healthcare consumer criteria for selecting a healthcare provider, the information comprising appointment time data and estimated wait time data associated with the at least one of the identified one or more healthcare providers that match at least one of the healthcare consumer criteria for selecting a healthcare provider.

19. The computer program product for selecting a healthcare provider of claim 18, wherein;

the one or more healthcare consumer criteria for selecting a healthcare provider comprises the criterion that the healthcare provider be the healthcare provider closest to a designated location in terms of distance.

20. The computer program product for selecting a healthcare provider of claim 18, wherein;

the one or more healthcare consumer criteria for selecting a healthcare provider comprises the criterion that the healthcare provider be the healthcare provider closest to a designated location in terms of time.

21. The computer program product for selecting a healthcare provider of claim 18, wherein;

obtaining available appointment time data and estimated wait time data from at least one of the identified one or more healthcare providers that match at least one of the healthcare consumer criteria for selecting a healthcare provider comprises obtaining available appointment time data associated with a given one of the at least one of the identified one or more healthcare providers that match at least one of the healthcare consumer criteria for selecting a healthcare provider from a computing system implemented application running on the given healthcare provider's computing system.

22. The computer program product for selecting a healthcare provider of claim 18, wherein;

obtaining available appointment time data and estimated wait time data from at least one of the identified one or more healthcare providers that match at least one of the healthcare consumer criteria for selecting a healthcare provider comprises obtaining estimated wait time data associated with a given one of the at least one of the identified one or more healthcare providers that match at least of the healthcare consumer criteria for selecting a healthcare provider from a computing system implemented application running on the given healthcare provider's computing system.

23. The computer program product for selecting a healthcare provider of claim 22, wherein;

the estimated wait time data for the given healthcare provider is determined based on a time difference between when a designated event occurs at the healthcare provider location for a specific appointment and when the designated event should have occurred at the healthcare provider location for the specific appointment.

24. The computer program product for selecting a healthcare provider of claim 23, wherein;

the computer program code, encoded on the computer readable medium, further comprises computer readable instructions for:

providing the healthcare consumer with the capability to make a selected appointment with a selected one of the at least one of the identified one or more healthcare providers that match at least one of the healthcare consumer criteria for selecting a healthcare.

25. A method for selecting a healthcare provider comprising:
- obtaining a list of one or more healthcare providers, the list of one or more healthcare providers comprising information associated with one or more healthcare providers;
- a healthcare consumer initiating a healthcare provider search request;
- in response to the healthcare consumer initiated healthcare provider search request, providing access to data representing the list of one or more healthcare providers;
- in response to the healthcare consumer initiated healthcare provider search request, searching the list of one or more healthcare providers to identify one or more healthcare providers that are closest to a location designated by the healthcare consumer, the process operable to match criteria including one or more geographical areas to exclude from search results thus ensuring that no providers located within the excluded geographical areas are included within the identified one or more healthcare providers, the one or more geographical areas to exclude being provided in the search request;
- obtaining available appointment time data and estimated wait time data from one or more of the identified one or more healthcare providers that are closest to the location designated by the healthcare consumer;
- providing the healthcare consumer with the ability to select one of the at least one of the identified one or more healthcare providers that are closest to a location designated by the healthcare consumer; and
- automatically making the next available appointment with the selected one of the at least one of the identified one or more healthcare providers that are closest to a location designated by the healthcare consumer.

* * * * *

UNITED STATES PATENT AND TRADEMARK OFFICE
CERTIFICATE OF CORRECTION

PATENT NO.        : 8,060,500 B1                                    Page 1 of 1
APPLICATION NO.   : 12/018076
DATED             : November 15, 2011
INVENTOR(S)       : Todd M. Fitch et al.

It is certified that error appears in the above-identified patent and that said Letters Patent is hereby corrected as shown below:

In the Claims

In Column 35, Lines 20-21, Claim 1, replace "at least of the" with --at least one of the--;
In Column 36, Line 44, Claim 12, replace "comprise" with --comprises--;
In Column 37, Line 26, Claim 16, after "healthcare provider", insert --;--;
In Column 37, Line 33, Claim 16, between "directions to" and "healthcare provider", insert --the--;
In Column 37, Lines 58-59, Claim 18, replace "at least of the" with --at least one of the--;
In Column 38, Lines 48-49, Claim 22, replace "at least of the" with --at least one of the--; and
In Column 39, Line 3, Claim 24, between "healthcare" and ".", insert --provider--.

Signed and Sealed this
Twenty-fifth Day of March, 2014

Michelle K. Lee
*Deputy Director of the United States Patent and Trademark Office*